United States Patent [19]
Castillo

[11] Patent Number: 5,135,469
[45] Date of Patent: Aug. 4, 1992

[54] POST-SURGICAL KNEE BRACE WITH INCREMENTAL ADJUSTMENT

[75] Inventor: Edward L. Castillo, Mission Viejo, Calif.

[73] Assignee: Innovation Sports, Inc., Irvine, Calif.

[21] Appl. No.: 694,927

[22] Filed: May 2, 1991

[51] Int. Cl.⁵ .............................................. A61F 5/00
[52] U.S. Cl. ...................................... 602/16; 602/23; 602/26; 602/20
[58] Field of Search ................ 128/80 B, 80 C, 80 F, 128/77, 88

[56] References Cited

U.S. PATENT DOCUMENTS

| | | | |
|---|---|---|---|
| 3,099,448 | 7/1963 | Salvo et al. | 128/88 |
| 4,271,831 | 6/1981 | Deibert | 128/80 C |
| 4,614,181 | 9/1986 | Karlsson | 128/80 F |
| 4,886,054 | 12/1989 | Castillo et al. | 128/80 F |
| 4,964,402 | 10/1990 | Grim et al. | 128/80 H |

*Primary Examiner*—Richard J. Apley
*Assistant Examiner*—Lynne Reichard
*Attorney, Agent, or Firm*—Stetina and Brunda

[57] ABSTRACT

A brace for supporting a knee joint is disclosed which is specifically adapted for use in post-surgical applications. The brace is formed by an upper pair of struts and a lower pair of struts which are disposed on opposite sides of the knee joint and which include end portions which are pivotally connected by way of ratio-swing hinge members. A plurality of cuffs are provided which are used to interconnect the struts comprising the upper pair and the lower pair. Means are additionally provided to adjust the position of an upper strut and lower strut relative the cuffs.

13 Claims, 2 Drawing Sheets

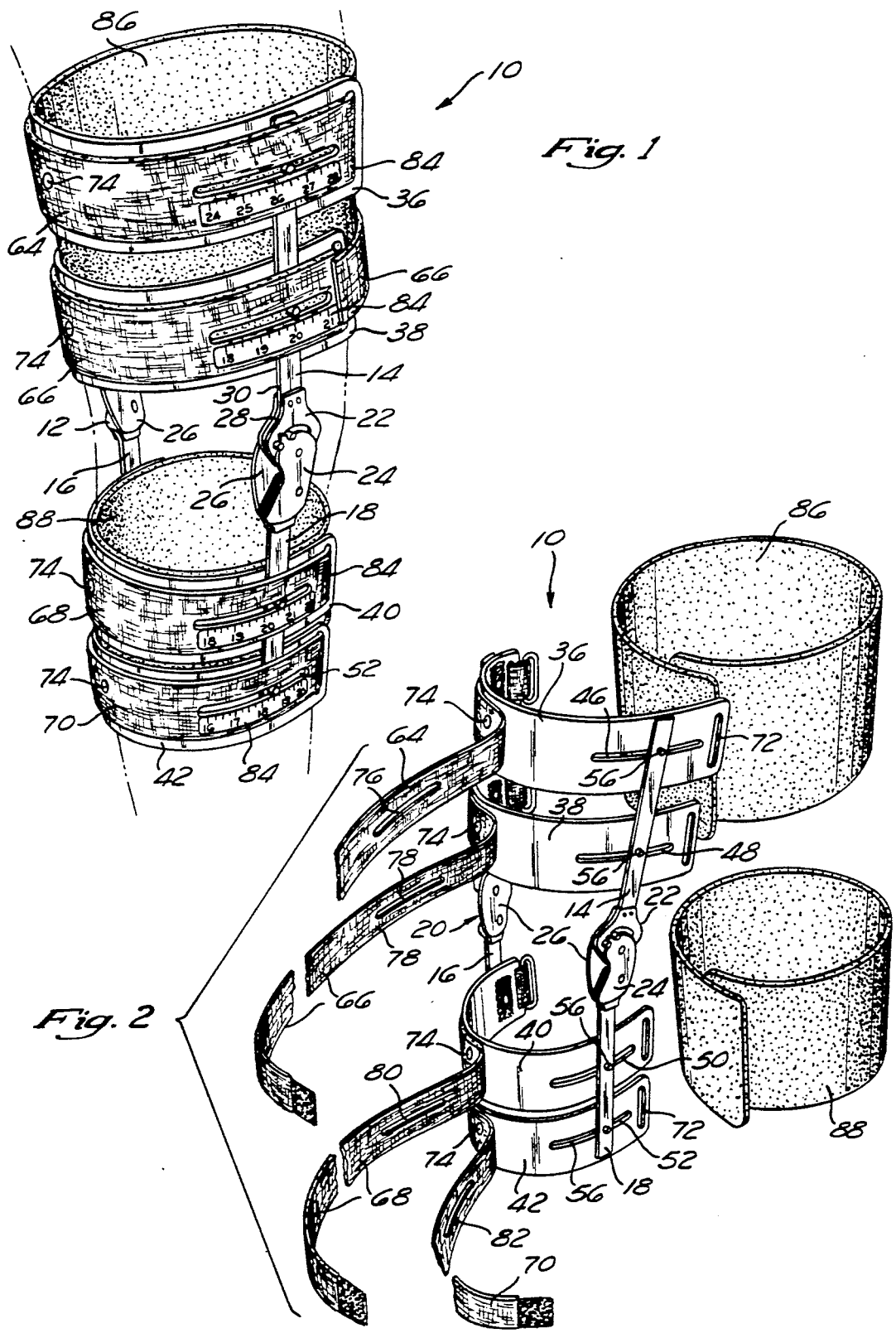

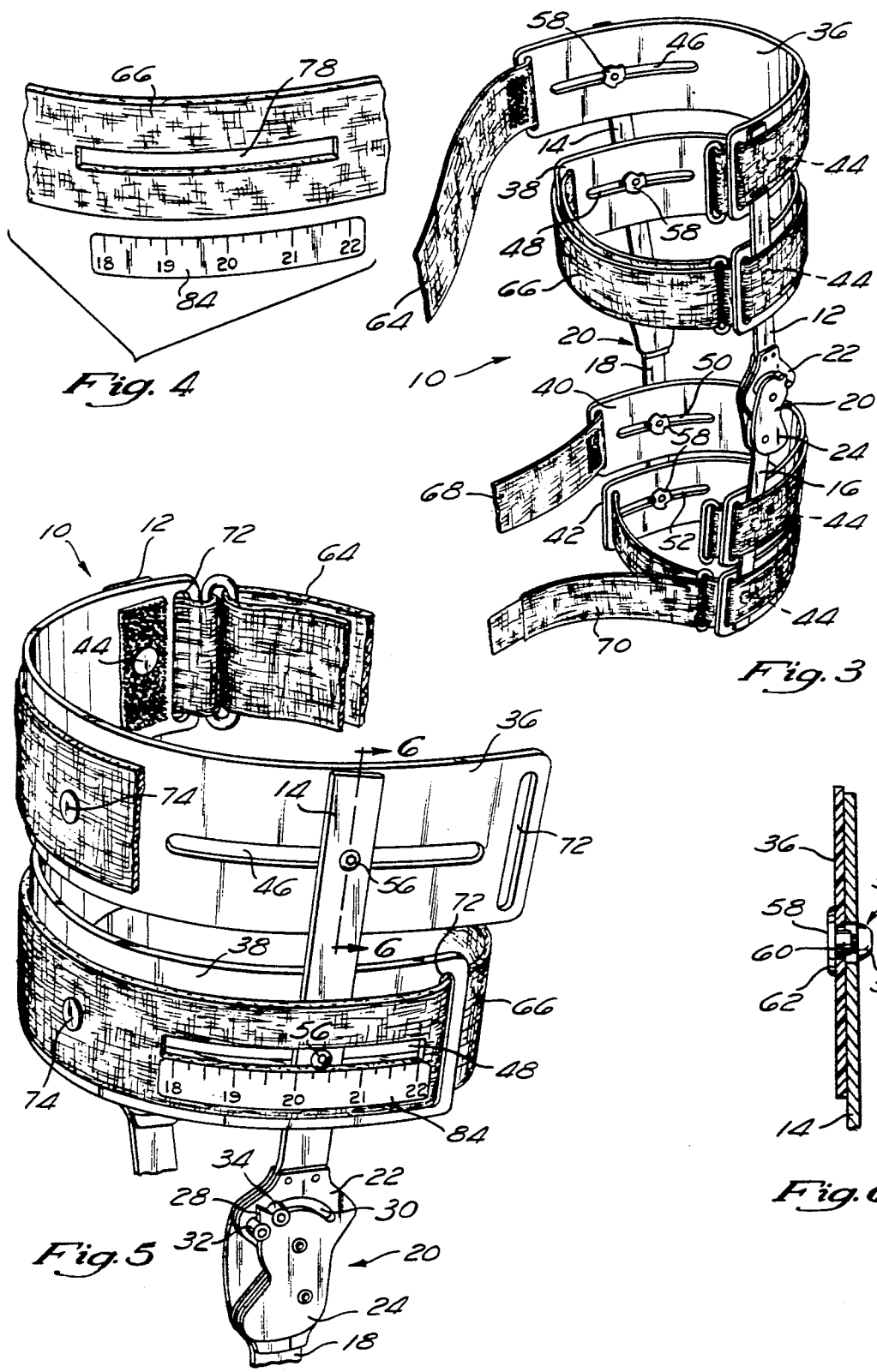

POST-SURGICAL KNEE BRACE WITH INCREMENTAL ADJUSTMENT

FIELD OF THE INVENTION

The present invention relates to braces for supporting joints, and more particularly to a post-surgical knee brace which is adapted to be incrementally adjustable so as to be easily and quickly adaptable to a user's leg.

BACKGROUND OF THE INVENTION

As is well known, the knee joint, although frequently considered a hinge joint, actually comprises two joints, lateral and medial, between the femur and tibia, and one arthrodial joint between the patella and femur. The primary movements of the knee comprise flexion, i.e. rearward rotational movement of the tibia relative the femur, and extension, i.e. forward rotational movement of the tibia relative the femur.

The flexion and extension movements of the knee joint are not simply pivotal movements about a fixed axis. During flexion, the axis around which movement takes place shifts backward, and during extension it shifts forward. This is different from a more typical hinge joint, such as an elbow, where the axis of rotation does not shift. As full extension is reached, the tibia is rotated inward or rearward and the joint in effect is disposed in a "locked" position with the ligaments taut. This gives the joints greater stability in the extended position. As flexion is initiated, the tibia initially lowers or moves downwardly with the small external rotation of the tibia which "unlocks" the joint and subsequently the tibia rotates or rolls about the joint to full flexion. Accordingly, the initial unlocking of the knee joint during flexion proceeds actual full rotation of the knee.

Due to the above complexity of knee movement, for a knee brace to more fully support the knee joint of the user and facilitate rehabilitation and/or prevent re-injury of an injured knee joint, the brace must more closely analogize the movement of the knee than a simple hinge mechanism. With specific relation to post-surgical applications, the requirement for such analogized movement becomes acute for the proper rehabilitation of the knee joint. Additionally, for such post-surgical applications, the knee brace should be relatively lightweight to avoid overly hindering the user's mobility yet possess sufficient structural strength to adequately support the knee joint during rehabilitation. Further, knee braces used in conjunction with such surgical applications should be easily and quickly adjustable to conform to the particular size of the user's leg and to maintain such adjusted size so that the knee brace may be removed from the leg during bathing and showering and subsequently reattached to the leg with a minimum amount of difficulty.

In recognizing the need for an effective post-surgical knee brace, various knee braces have been introduced into the marketplace. Such contemporary knee braces, however, have generally failed to provide the precise simulation of knee joint movement as described above or have comprised relatively heavy, bulky apparatus, thereby detracting from the user's mobility while wearing the brace. Further, such contemporary designs have typically failed to possess sufficient adjustability so as to be quickly and easily interfaceable to the leg of the user or to maintain an adjusted configuration so as to permit periodic removal and reattachment of the knee brace to the user's leg.

SUMMARY OF THE INVENTION

The present invention specifically addresses and alleviates the above-referenced deficiencies associated with the prior art. More particularly, the present invention comprises a lightweight, adjustable brace for supporting a knee joint which, although not limited thereto, is specifically adapted for use in post-surgical applications.

The knee brace is formed by an upper pair of struts and a lower pair of struts which are positioned in an inverted, relative orientation above and below the knee joint of a user with the end portions of the upper pair and lower pair being disposed laterally on opposite sides of the knee joint. A pair of ratio-swing hinge members disposed substantially adjacent the knee joint are used to connect the end portions of the upper pair of struts and the lower pair of struts such that the upper pair and lower pair may be pivoted about the knee joint. The ratio-swing hinge members are specifically designed to closely simulate rotational movement of the tibia relative the femur whereby the pivot point of the hinge varies or changes during rotational movement of the tibia relative the femur. As such, the knee brace of the present invention closely simulates normal knee movement, thereby enhancing rehabilitation and preventing injury to the knee during use. Each of the struts comprising the upper pair and the lower pair are preferably formed of stainless steel so as to have sufficient strength to adequately support the knee joint during rehabilitation.

In the preferred embodiment, first and second cuff members interconnect the upper pair of struts and third and fourth cuff members interconnect the lower pair of struts. Each of the four cuff members has a generally arcuate configuration and is sized to be disposed adjacent a particular portion of the rear of the user's leg. Additionally, each of the cuff members is preferably formed of plastic so as to make the knee brace sufficiently lightweight so as not to hamper the mobility of the user. Each of the four cuff members further includes a strap member mounted thereto to facilitate the attachment of the knee brace to the user's leg. As will be recognized, the two strap members mounted to the two cuff members interconnecting the upper struts are extensible about the front of the user's thigh while the two strap members mounted to the two cuff members interconnecting the lower struts are extensible about the front of the user's calf.

For the knee brace to function properly in the rehabilitation of the knee joint, the upper and lower pairs of struts are preferably disposed laterally on opposite sides of the knee joint such that the hinge members are disposed substantially adjacent the knee joint. Accordingly, the present invention incorporates means associated with the cuff members for selectively positioning the upper pairs of struts and the lower pair of struts relative the knee joint to achieve the aforementioned alignment characteristics. In the preferred embodiment, the positioning means comprises elongate slots disposed in each of the four cuff members. These slots are adapted to allow an upper strut and a lower strut connected via one of the ratio-swing hinge members to be slidably positionable relative the cuff members to which they are interfaced. Additionally, each of the strap members includes a slot disposed therein which is adapted to be in general alignment with the slot disposed in the cuff to which the strap is mounted. Further, each strap includes indicia thereon adjacent the slot disposed therein to aid in the precise positioning of the interconnected upper and lower struts relative their respective cuffs.

To prevent any hyper-extension of the knee joint during use, the knee brace of the present invention incorporates a unique stop mechanism into the ratio-swing hinges. In the preferred embodiment, the stop mechanism comprises stop inserts which are interfaced to the hinges and may be used to control the amount of flexion and/or extension of the knee joint. Additionally, the stop members may be manipulated such that extension of the knee joint is unrestricted.

The present invention also incorporates pad members which are connected to the cuffs and used to provide a cushion between the user's leg and the plastic cuffs of the knee brace.

BRIEF DESCRIPTION OF THE DRAWINGS

These as well as other features of the present invention will become more apparent upon reference to the drawings wherein:

FIG. 1 is a rear perspective view of the knee brace of the present invention as interfaced to a leg of the user;

FIG. 2 is a front perspective view of the knee brace of the present invention;

FIG. 3 is a front perspective view of the knee brace of the present invention;

FIG. 4 is a partial perspective view illustrating a slot disposed within a strap member and the indicia attachable to the strap member adjacent the slot;

FIG. 5 is a partial perspective view of the upper portion of the knee brace of the present invention; and FIG. 6 is a cross-sectional view taken along line 6—6 of FIG. 5.

DETAILED DESCRIPTION OF THE PREFERRED EMBODIMENT

The description set forth below in connection with the appended drawings is intended merely as a description of the presently preferred embodiment of the invention, and is not intended to represent the only form in which the present invention may be utilized. The description sets forth the functions and structural elements of the invention in connection with the illustrated preferred embodiment. It will be understood however that the same or equivalent functions and advantages of the present invention may be accomplished by different embodiments which are encompassed within the spirit and scope of the present invention.

Referring to the drawings, the knee brace 10 of the present invention, specifically adapted for post-surgical applications, is depicted. For purposes of illustration, the knee brace 10 is illustrated in a right-leg embodiment which is adapted to be worn upon the right leg of a user. However, it will be recognized that the invention is additionally applicable to left-leg embodiments with the structure of the brace 10 being the same but reversed in orientation. As best shown in FIGS. 1-3, the knee brace 10 is composed of an upper pair of struts comprising a medial upper strut 12 and a lateral upper strut 14 and a lower pair of struts comprising a medial lower strut 16 and a lateral lower strut 18. The upper pair of struts 12 and 14 and the lower pair of struts 16 and 18 are disposed in an inverted relative orientation and positionable on opposite sides of the knee joint of a user. In the preferred embodiment, each strut is formed from stainless steel so as to have sufficient rigidity to support the knee joint during rehabilitation. However, other materials possessing sufficient strength and rigidity are contemplated herein.

The connection of lateral upper strut 14 to lateral lower strut 18 and medial upper strut 12 to medial lower strut 16 is facilitated by a pair of ratio-swing hinges 20, each composed generally of an upper hinge component 22 and a lower hinge component 24 which are interconnected by a plate member 26. As seen in FIGS. 1-3 and 5, the upper hinge components 22 are mounted to the lateral upper strut 14 and the medial upper strut 12 while the lower hinge components 24 are mounted to the lateral lower strut 18 and the medial lower strut 16. In the preferred embodiment, plate member 26 is pivotally mounted to upper hinge component 22 and lower hinge component 24. Due to the pivotal connection of plate member 26 to upper hinge component 22 and lower hinge component 24, ratio-swing hinges 20 allow relative movement of the upper struts 12 and 14 and lower struts 16 and 18 in a regulated manner varying pivot axis which simulates normal knee movement wherein during initial movement of the tibia relative the femur in flexion, the tibia slightly lowers to open "unlock" the knee joint and once "unlocked" subsequently pivots rapidly backward in flexion. In the preferred embodiment, the upper hinge component 22, lower hinge component 24, and plate member 26 are formed of stainless steel, though it will be appreciated that other materials may be utilized.

A more thorough description of the operational principles of the ratio-swing hinges 20 is disclosed in U.S. Pat. No. 4,940,044, issued Jul. 10, 1990, and assigned to the assignee of the subject application, the disclosure of which is expressly incorporated herein by reference. Although in the preferred embodiment the present invention utilizes the ratio-swing hinges 20, those skilled in the art will recognize that other hinge designs may be substituted therefore and are contemplated herein.

As seen in FIGS. 1 and 5, formed on lower hinge component 24 is a pointed extension 28 and disposed within upper hinge component 22 is a generally arcuate slot 30. Disposed within slot 30 on either side of extension 28 are a first stop member 32 and a second stop member 34 which are selectively positionable within slot 30. As can be appreciated, stop members 32 and 34 are used to control the relative pivotal movement between upper struts 12 and 14 and lower struts 16 and 18 by limiting the distance extension 28 may travel relative slot 30. In this respect, by selectively positioning stop members 32 and 34 within slot 30, the amount of flexion and/or extension to which the knee joint may be subjected can be controlled. Additionally, by removing first stop member 32 from within slot 30, knee brace 10 may provide the knee joint with unlimited extension. In traditional rehabilitation practices, the knee joint is not permitted to go to full extension, but rather is limited to movement within the range of 35 to 45 degrees of full extension. However, newly emerging rehabilitation practices have recognized the benefit of permitting the knee joint undergoing rehabilitation to be fully extended. As such, the knee brace 10 of the present invention recognizes the desirability of allowing the knee to achieve full extension by providing the stop members 32 and 34 in the aforementioned configuration.

Referring to FIGS. 1-3 and 5, interconnecting lateral upper strut 14 and medial strut 12 are a first cuff 36 and a second cuff 38, each of which has a generally arcuate configuration so as to be positionable adjacent the rear of the user's leg, i.e. the thigh. Similarly, interconnecting lateral lower strut 18 and medial lower strut 16 are a third cuff 40 and a fourth cuff 42 which also have generally arcuate configurations so as to be positionable adjacent the rear of the user's leg, i.e. the calf. If the preferred embodiment, cuffs 36, 38, 40, and 42 are all constructed from plastic so as to make knee brace 10 lightweight, though other materials are contemplated herein. Medial upper strut 12 is rigidly affixed to cuffs 36 and 38 and medial lower strut 16 is rigidly affixed to cuffs 40 and 42 via rivets 44. As previously indicated, for knee brace 10 to function properly, it is essential that the upper struts 12 and 14 and the lower struts 16 and 18, and hence the hinge members 20, be disposed laterally on opposite sides of the knee joint. In this respect, to properly position the knee brace 10 about the knee joint of the user, lateral upper strut 14 is adapted to be slidably positionable relative cuffs 36 and 38 and lateral lower strut 18 is adapted to be slidably positionable relative cuffs 40 and 42. As will be recognized, the adjustability of struts 14 and 18, relative their respective cuffs, allows knee brace 10 to be quickly and easily sized in accordance with the particular requirements of a user. To facilitate such slidability, disposed within first cuff 36 is a first slot 46 and disposed within second cuff 38 is a second slot 48. Additionally, disposed within third cuff 40 is a third slot 50 and disposed within fourth cuff 42 is a fourth slot 52. In the preferred embodiment, the interface of lateral upper strut 14 to slots 46 and 48 and lateral lower strut 18 to slots 50 and 52 is facilitated by connectors 54. As best see in FIG. 6, each of connectors 54 generally comprises a screw 56 which is threadably received into a lock member 58. Lock member 58 comprises a cylindrical portion 60 which is sized and configured to be slidably received into a slot disposed within a cuff, and a flange portion 62 which is adapted to abut the inner surface of a cuff. As will be appreciated, when connectors 54 are loosened, lateral upper strut 14 is slidably positionable relative cuffs 36 and 38 and lateral lower strut 18 is slidably positionable relative cuffs 40 and 42. Additionally, when connectors 54 are tightened, lateral upper strut 14 and lateral lower strut 18 are retained in a particular orientation relative their respective cuffs.

As shown, the knee brace 10 of the present invention is preferably attached to the user's leg via strap members 64, 66, 68, and 70. Preferably, strap members 64 and 66 are mounted directly to cuffs 36 and 38, respectively, and are adapted to extend about the front of the user's thigh. Strap members 68 and 70 are preferably mounted directly to cuffs 40 and 42, respectively, and are adapted to extend about the front of the user's calf. Each of the strap members are preferably received into vertical slots 72 disposed within the opposed ends of each cuff and are rigidly mounted to each cuff via fasteners, such as rivets 74. As seen in FIGS. 1-2 and 4-5, strap members 64 and 66 include slots 76 and 78 therein, and strap members 68 and 70 include slots 80 and 82 therein. Strap members 64 and 66 are mounted to cuffs 36 and 38 in a manner such that when wrapped about the thigh of the user, slot 76 is generally aligned with slot 46 and slot 78 is generally aligned with slot 48. Similarly, strap members 68 and 70 are mounted to cuffs 40 and 42 in a manner such that when wrapped about the calf of the user, slot 80 is generally aligned with slot 50 and slot 82 is generally aligned with slot 52.

Referring now to FIGS. 1, 4, and 5, strap members 64, 66, 68, and 70 each include measurement indicia adjacent the respective slot disposed therein. As best seen in FIG. 4, the measurement indicia preferably takes the form of a label 84 which is applied to each strap member so as to be oriented below the slot disposed therein. In the preferred embodiment, the measurement indicia is used to aid in the positioning of the lateral upper strut 14 and lateral lower strut 18 such that the hinge members 20 are disposed laterally on opposite sides of the knee joint. In this respect, by taking measurements of various portions of the user's thigh and calf, the indicia may be used to achieve a precise separation of the lateral and medial struts and hence the hinge members 20 so that knee brace 10 functions properly when worn by the user. Though not shown, to allow adjustment of the strap members 64, 66, 68, and 70, an adjustment member and clasp may be provided on such strap members.

As seen in FIGS. 1 and 2, knee brace 10 of the present invention further includes a thigh pad 86 and a calf pad 88 which are adapted to be wrapped around the leg of the user. Pad 86 and pad 88 are preferably fabricated from a foam rubber material, and are releasably attachable to the inner surfaces of the cuffs 36, 38, 40, and 42 via velcro fasteners disposed on the inner surfaces of the cuffs. As will be recognized, pads 86 and 88 serve as a cushion between the user's leg and the knee brace 10.

With the structure defined, the operation of the knee brace 10 of the present invention may be described. Initially, measurements of portions of the user's thigh and calf are taken prior to surgery. Such measurements are taken before surgery since no swelling to the user's leg or knee has yet occurred. Connectors 54 are then loosened so as to allow lateral upper strut 14 and lateral lower strut 18 to be slidably positioned relative their respective cuffs. Due to the inclusion of the measurement indicia on label 84 attached to each of the strap members, the lateral upper strut 14 and lateral lower strut 18 may be positioned based on the measurements taken of the user's leg such that the hinge members 20 will be disposed laterally on opposite sides of the knee joint when the knee brace 10 is interfaced to the user's leg. When the precise degree of separation between hinge members 20 has been obtained, connectors 54 are then tightened so as to maintain lateral upper strut 14 and lateral lower strut 18 in their respective orientations.

With the proper size of brace 10 chosen, thigh pad 86 and calf pad 88 are then wrapped about the user's leg. Cuffs 36 and 38 are then positioned upon thigh pad 86 and cuffs 38 and 40 are positioned upon calf pad 88. When the knee brace 10 is positioned in this manner, the strap members 64 and 66 are firmly affixed about the user's thigh and strap members 68 and 70 are firmly affixed about the user's calf. As will be recognized, strap members 64 and 66 do not directly contact the user's thigh, but rather contact thigh pad 86 and strap members 68 and 70 do not directly contact the user's calf, but rather contact calf pad 88.

With the knee brace 10 of the present invention positioned upon the user's leg in this manner, the stop members 32 and 34 may be selectively positioned within hinge members 20 so as to limit the flexion and/or extension of the knee joint. Additionally, stop members 32 may be removed from hinge members 20 so as to permit slight hyperextension of the knee joint.

Although for purposes of illustration, certain materials, components, and structural embodiments have been depicted, those skilled in the art will recognize that various modifications to the same can be made without departing from the spirit of the present invention, and such modifications are clearly contemplated herein.

What is claimed is:

1. A post-surgical knee brace comprising:
   an upper pair of struts and a lower pair of struts, said upper pair and said lower pair being positionable in an inverted, relative orientation above and below the knee joint of a user with the end portions of said upper pair and said lower pair being disposed laterally on opposite sides of the knee joint;
   a pair of hinge members disposed substantially adjacent the knee joint and connected to the end portions of the upper pair and lower pair to pivot the upper pair and lower pair about the knee joint;
   at least one upper cuff interconnecting said upper pair of struts and disposed adjacent the rear of the user's leg;
   at least one lower cuff interconnecting said lower pair of struts and disposed adjacent the rear of the user's leg;
   a first slot disposed in said upper cuff for allowing a first lateral strut of said upper pair to be slidably positionable relative said upper cuff; and
   a second slot disposed in said lower cuff for allowing a second lateral strut of said lower pair to be slidably positionable relative said lower cuff;
   said first lateral strut and said second lateral strut being interconnected by one of said hinge members and being selectively positionable relative the knee joint via said first and second slots.

2. The knee brace of claim 1 further comprising;
   at least one upper strap mounted to said upper cuff and extensible about the front of the user's thigh; and
   at least one lower strap mounted to said lower cuff and extensible about the front of the user's calf.

3. The knee brace of claim 2 further comprising an upper slot disposed in said upper strap so as to be in general alignment with said first slot when said upper strap is mounted to said upper cuff, said upper strap further including indicia thereon adjacent said upper slot to selectively position the first lateral strut relative the upper cuff.

4. The knee brace of claim 3 further comprising a lower slot disposed in said lower strap so as to be in general alignment with said second slot when said lower strap is mounted to said lower cuff, said lower strap further including indicia thereon adjacent said lower slot to selectively position the second lateral strut relative the lower cuff.

5. The knee brace of claim 1 further comprising means formed on said pair of hinge members for regulating the relative pivotal movement of said upper pair of struts and said lower pair of struts.

6. The knee brace of claim 5 further comprising means formed on said pair of hinge members for limiting the extension of said upper pair of struts and said lower pair of struts.

7. The knee brace of claim 1 further comprising a first pad releasably attachable to said upper cuff and a second pad releasably attachable to said lower cuff, said first and second pads being adapted to provide a padded interface between said upper and lower cuffs and the user's leg.

8. A post-surgical brace comprising:
   an upper pair of struts and a lower pair of struts, said upper pair and said lower pair being positionable in an inverted, relative orientation above and below the knee joint of a user with the end portions of said upper pair and said lower pair being disposed laterally on opposite sides of the knee joint;
   a pair of hinge members disposed substantially adjacent the knee joint and connected to the end portions of the upper pair and lower pair to pivot the upper pair and lower pair about the knee joint;
   a first cuff and a second cuff interconnecting said upper pair of struts and disposed adjacent the rear of the user's thigh;
   a third cuff and fourth cuff interconnected said lower pair of struts and disposed adjacent the rear of the user's calf;
   a first slot disposed in said first cuff and a second cuff disposed in said second cuff, said first and second slots being adapted to allow a first lateral strut of said upper pair to be slidably positionable relative said first and second cuffs; and
   a third slot disposed in said third cuffs and a fourth slot disposed in said fourth cuff, said third and fourth slots being adapted to allow a second lateral strut comprising said lower pair to be slidably positionable relative said third and fourth cuffs;
   said first lateral strut and said second lateral strut being interconnected by one of said hinge members and being slidably positionable relative said first, second, third, and fourth cuffs via said first, second, third, and fourth slots.

9. The knee brace of claim 8 further comprising:
   a first strap mounted to said first cuff and a second strap mounted to said second cuff, said first and second straps being extensible about the front of the user's thigh; and
   a third strap mounted to said third cuff and a fourth strap mounted to said fourth cuff, said third and fourth straps being extensible about the front of the user's calf.

10. The knee brace of claim 9 further comprising a fifth slot disposed in said first strap and a sixth slot disposed in said second strap, said fifth and sixth slots being in general alignment with said first and second slots, respectively, when said first strap is mounted to said first cuff and said second strap is mounted to second cuff, said first strap and said second strap further including indicia thereon adjacent said fifth and sixth slots to selectively position the first lateral strut relative the first and second cuffs.

11. The knee brace of claim 10 further comprising a seventh slot disposed in said third strap and an eighth slot disposed in said fourth strap, said seventh and eighth slots being in general alignment with said third and fourth slots, respectively, when said third strap is mounted to said third cuff and said fourth strap is mounted to said fourth cuff, said third and fourth straps further including indicia thereon adjacent said seventh and eighth slots to selectively position the second lateral strut relative the third and fourth cuffs.

12. A post-surgical knee brace comprising:
    an upper pair of struts and a lower pair of struts, said upper pair and said lower pair being positionable in an inverted, relative orientation above and below the knee joint of a user with the end portions of said upper pair and said lower pair being disposed laterally on opposite sides of the knee joint;

a pair of hinge members disposed substantially adjacent the knee joint and connected to the end portions of the upper pair and lower pair to pivot the upper pair and lower pair about the knee joint;

at least one upper cuff interconnecting said upper pair of struts and disposed adjacent the rear of the user's leg; and at least one lower cuff interconnecting said lower pair of struts and disposed adjacent the rear of the user's leg;

said upper and lower cuffs being slidably connected to said upper and lower pairs of struts and including indicia associated therewith so as to allow said upper pair and said lower pair to be selectively positionable laterally relative the knee joint.

13. The knee brace of claim 12 further comprising means formed on said pair of hinge members for regulating the relative pivotal movement of said upper pair of struts and said lower pair of struts.

* * * * *